United States Patent
Xu et al.

(10) Patent No.: US 11,891,411 B2
(45) Date of Patent: Feb. 6, 2024

(54) **INDUSTRIAL UTILIZATION METHOD FOR *STEVIA REBAUDIANA* AND STEVIOSIDE AND CHLOROGENIC ACID OF *STEVIA REBAUDIANA***

(71) Applicant: Chenguang Biotech Group Co., Ltd., Hebei (CN)

(72) Inventors: Meili Xu, Hebei (CN); Yunhe Lian, Hebei (CN); Hong Tian, Hebei (CN); Wei Gao, Hebei (CN); Yachao Xu, Hebei (CN)

(73) Assignee: Chenguang Biotech Group Co., Ltd., Hebei (CN)

( * ) Notice: Subject to any disclaimer, the term of this patent is extended or adjusted under 35 U.S.C. 154(b) by 186 days.

(21) Appl. No.: 17/216,928

(22) Filed: Mar. 30, 2021

(65) Prior Publication Data

US 2021/0230204 A1 Jul. 29, 2021

Related U.S. Application Data

(63) Continuation of application No. PCT/CN2019/108619, filed on Sep. 27, 2019.

(30) Foreign Application Priority Data

Sep. 30, 2018 (CN) .......................... 201811159791.7

(51) Int. Cl.
*C07H 15/24* (2006.01)
*C07C 67/56* (2006.01)

(52) U.S. Cl.
CPC ............. *C07H 15/24* (2013.01); *C07C 67/56* (2013.01)

(58) Field of Classification Search
CPC ................... C07H 15/24; C07C 67/56
See application file for complete search history.

(56) References Cited

FOREIGN PATENT DOCUMENTS

| CN | 101062077 | 10/2007 |
|---|---|---|
| CN | 101062078 | 10/2007 |
| CN | 101798329 | 8/2010 |
| CN | 102617667 | 7/2014 |
| CN | 106236808 | 12/2016 |
| CN | 106674307 | 5/2017 |
| CN | 105001281 | 2/2018 |
| CN | 109293712 | 2/2019 |
| WO | WO 2008/122990 | 10/2008 |

OTHER PUBLICATIONS

Machine translation of CN102617667A, description and claims, 7 pages, originally published Jul. 2014 (Year: 2014).*
Machine translation of CN106236808A, description and claims, 7 pages, originally published Dec. 2016 (Year: 2016).*
Machine translation of CN106674307A, description and claims, 4 pages, originally published May 2017 (Year: 2017).*
Fiamegos, et al., "Antimicrobial and efflux pump inhibitory activity of caffeoylquinic acids from Artemisia absinthium against gram-positive pathogenic bacteria", PLoS One, 6 (4), 18127, 2011.
Harrison, Jr. et al., "Contents of Caffeoylquinic Acid Compounds in the Storage Roots of Sixteen Sweetpotato Genotypes and Their Potential Biological Activity", JASHS, 133 (4), 492, 2008.
Iwai et al., "In vitro antioxidative effects and tyrosinase inhibitory activities of seven hydroxycinnamoyl derivatives in green coffee beans," J. Agric. Food Chem., 52 (15), 4893, 2004.
Ooi et al., "Antiviral activities of purified compounds from *Youngia japonica* (L.) DC (Asteraceae, Compositae)", J. Ethnopharmacol, 106 (2), 187, 2006.
Peluso et al., "Studies on the Inhibitory Effects of Caffeoylquinic Acids on Monocyte Migration and Superoxide Ion Production", J. Nat. Prod., 58, 5, 639-646, 1995.
Zhang et al, "3,5-Dicaffeoylquinic acid isolated from Artemisia argyi and its ester derivatives exert anti-Leucyl-tRNA synthetase of Giardia lamblia (GILeuRS) and potential anti-giardial effects", Fitoterapia, 83, 1281-1285, 2012.
Zhang Li-na et al., "Reaserch on extraction and purification of stevioside from stevia leaves," China Condiment, No. 1, Jan. 2008.

* cited by examiner

*Primary Examiner* — Bahar Craigo
(74) *Attorney, Agent, or Firm* — Levine Bagade Han LLP

(57) ABSTRACT

An industrialization method for comprehensive utilization of *Stevia rebaudiana*. The major improvement is in that the *Stevia rebaudiana* is extracted by using a high-concentration alcohol solution, then the extracted solution is purified by using an organic solvent, and the pH of the extracted solution is adjusted to be alkaline according to the acidic characteristic of chlorogenic acid to enable the chlorogenic acid to be formed into a salt and have an increased polarity so as to achieve effective separation of the chlorogenic acid and a glucoside component in an adsorption process. The method allows the high-quality stevioside and chlorogenic acid to be obtained, significantly improves the comprehensive utilization rate of *Stevia rebaudiana*, reduces the waste of natural *Stevia rebaudiana* resources, reduces the resource consumption in a production process, reduces waste discharge, and is a high-benefit green production process.

12 Claims, No Drawings

INDUSTRIAL UTILIZATION METHOD FOR *STEVIA REBAUDIANA* AND STEVIOSIDE AND CHLOROGENIC ACID OF *STEVIA REBAUDIANA*

CROSS-REFERENCE TO RELATED APPLICATIONS

This application is a continuation of International Patent Application Number PCT/CN2019/108619 filed Sep. 27, 2019, which claims priority to Chinese Patent Application Number CN 201811159791.7 filed Sep. 30, 2018, the content of which is incorporated herein by reference in its entirety.

TECHNICAL FIELD

The present invention relates to the field of extraction of active ingredients in plants, and in particular to an industrialized method for the comprehensive utilization of chlorogenic acid and stevioside in *Stevia rebaudiana*.

BACKGROUND ART

*Stevia rebaudiana* belongs to a perennial herb of the Compositae family. *Stevia rebaudiana* is native to Paraguay and Brazil in south America, is currently known as one of the sugar plants with relatively high sweetness, and has become the third natural sugar source after sucrose and beet sugar. At present, China is the world's largest producer and supplier of stevioside, accounting for 80% and more of the global total yield. In addition to steviosides, *Stevia rebaudiana* also contains 3% to 6% of chlorogenic acid (HPLC), of which isochlorogenic acid accounts for nearly 80%, and isochlorogenic acid has important biological activities, such as anti-inflammation, anti-viral, anti-oxidation, lowering blood pressure, lowering blood lipids and the like. *Stevia rebaudiana* has been used as sweet tea and medicinal tea for more than one hundred years in its provenance.

Traditional *Stevia rebaudiana* industry uses water extraction, but isochlorogenic acid is prone to hydrolysis during the extraction process, such that the proportion of isochlorogenic acid in the water extract solution is greatly reduced, and the proportions of mono-caffeoylquinic acid and caffeic acid are greatly increased.

Studies have shown that isochlorogenic acid has many important biological effects, such as anti-oxidation (J. Agric. Food Chem., 2004, 52 (15), 4893), anti-inflammation (J. Nat. Prod., 1995, 58 (5), 639), anti-bacterial and anti-viral (JASHS, 2008, 133 (4), 492; Fitoterapia, 2012, 83, 1281; PLoS One, 2011, 6 (4), 18127; J. Ethnopharmacol, 2006, 106 (2), 187) and the like.

Patents CN 200710111313.4 and CN 200710111314.9 discloses extraction is performed with ethanol, after concentration, polyamide, AB-8 or HPD400 resins and the like are used for adsorption, and gradient desorption is performed to obtain glycosides and flavonoid products. In addition to glycosides and flavonoids in the alcohol extract, some low-polar impurities will also be extracted at the same time, and the removal of impurities is not carried out before resin purification, which will cause rapid pollution of the resin, and inclusion of some low-polar impurities in the *Stevia rebaudiana* alcohol extract. The desorption process with low-concentration ethanol solution can only remove high-polar impurities, and during the desorption with high-concentration ethanol solution, low-polar impurities enter the desorbed glycoside solution, which affects the quality of glycoside products such that the products fail to meet market requirements. Further, in these patents, chlorogenic acid cannot be obtained from *Stevia rebaudiana*.

SUMMARY OF THE INVENTION

The purpose of the present invention is to provide an industrial utilization method for *Stevia rebaudiana*, comprising:
1) extracting *Stevia rebaudiana* powder with a high-concentration short-chain alcohol aqueous solution to obtain an extract solution;
2) removing the short-chain alcohol in the extract solution, subjecting the extract solution to liquid-liquid extraction with an organic solvent, and taking water layer to obtain a low-polar impurity-removed extract solution;
3) adjusting pH of the low-polar impurity-removed extract solution to be alkaline, passing the extract solution through a stevioside adsorption resin to separate a stevioside extract.

Preferably, the present invention also includes the step of collecting and separating chlorogenic acid, which comprises adjusting pH of lower column solution obtained by passing the low-polar impurity-removed extract solution through a stevioside resin to be acidic, and passing the post-column solution through a chlorogenic acid adsorption resin to obtain chlorogenic acid extract.

In the present invention, *Stevia rebaudiana* powder is extracted with high-concentration short-chain alcohol, by which stevioside and chlorogenic acid in the *Stevia rebaudiana* powder can be fully extracted, and at the same time the damage to isochlorogenic acid caused by water extraction can be avoided. Stevioside molecules contain different numbers of glycosyl fragments, which are poor in fat solubility. Low-polar impurities in the extract solution can be removed by liquid-liquid extraction without affecting the yield of steviosides, which can effectively increase the adsorption efficiency of resin to stevioside. Moreover, adjusting the pH of the extract solution to be alkaline can convert chlorogenic acid into a salt, which will not compete with steviosides during the adsorption process, thereby effectively improving the purity and quality of steviosides.

Preferably, the stevioside adsorption resin used in the present application is a low-polar resin commonly used in the separation of steviosides, preferably T28, ADS-750, 69M, DM30, and 201-H.

Preferably, the chlorogenic acid adsorption resin used in the present application is a resin commonly used in the separation process of chlorogenic acid, preferably SP207, LX-17, LSA-12, and 200B.

The resins of T28, 69M, LX-17, LSA-12, and 200B of the present invention are commercially available from the special resin factory of Xi'an Lanxiao Technology Co., Ltd., ADS-750 resin is commercially available from Tulsion, and DM30 resin is commercially available from Amicogen (China) Biomedicine Co., Ltd., 201-H resin is commercially available from Jiangsu Suqing Water Treatment Engineering Group Co., Ltd., and the like, SP207 resin is commercially available from from Mitsubishi Chemical Corporation of Japan.

The *Stevia rebaudiana* powder of the present invention is a raw powder of *Stevia rebaudiana* prepared by conventional drying and pulverization steps.

Preferably, the short-chain alcohol in the high-concentration short-chain alcohol aqueous solution is selected from methanol, ethanol, propanol or any combination thereof. A volume fraction of the short-chain alcohol in the short-chain alcohol aqueous solution is 70% to 95%. Choosing the above extracting solution can not only fully extract the effective components of stevioside and chlorogenic acid in *Stevia rebaudiana*, but also protect the isochlorogenic acid such that the isochlorogenic acid will not be hydrolyzed due to extraction.

More preferably, the short-chain alcohol aqueous solution is an ethanol solution with a volume fraction of 70% to 85%, a methanol solution with a volume fraction of 80% to 95%, or a propanol solution with a volume fraction of 70% to 75%.

Preferably, the organic solvent is a low-polar organic solvent that is water insoluble.

More preferably, the organic solvent is selected from pentane, n-hexane, octane, diethyl ether or cyclohexane. The above-mentioned extractant can effectively remove low-polar impurities in the feed solution, improve the quality and purity of the stevioside extract, and prolong the service life of the stevioside resin.

Preferably, in the step 3), the pH of the low-polar impurity-removed extract solution is adjusted to 9 to 11. Under the above-mentioned pH conditions, phenolic acids in *Stevia rebaudiana* can be fully salified and increased in polarity, and adsorption of phenolic acids on the stevioside adsorption resin can be reduced, separation from stevioside can be achieved, and the quality of stevioside products can be improved. If the pH is too low, the salifying is insufficient, and if the pH is too high, the hydrolysis of chlorogenic acid may occur.

Preferably, the pH of the post-column solution obtained by passing the low-polar impurity-removed extract solution through a stevioside resin is adjusted to 2 to 3. Under the above pH conditions, the chlorogenic acid can be in a free molecular state, which is more conducive to enrichment.

Preferably, the extraction is performed at a material-liquid ratio of 1:3.5 to 1:6, and an extraction temperature of 20° C. to 80° C.

Preferably, the extraction is performed for 2 to 3 times, 0.5 h to 3 h for each extraction.

Under the above conditions, chlorogenic acid and phenolic substances of *Stevia rebaudiana* can be fully extracted without damaging the active ingredients.

Preferably, the extraction method is one of leaching, spraying, and continuous countercurrent extraction.

As a preferred embodiment of operation, it comprises:
1) extracting *Stevia rebaudiana* powder with a high-concentration short-chain alcohol aqueous solution to obtain an extract solution;
2) removing the short-chain alcohol in the extract solution by vacuum concentration, subjecting a short-chain alcohol-removed extract solution to liquid-liquid extraction with an organic solvent, and taking water layer to obtain a low-polar impurity-removed extract solution;
3) adjusting pH of the low-polar impurity-removed extract solution to be alkaline, passing the extract solution through a stevioside adsorption resin for adsorption, subjecting the stevioside adsorption resin to elution with water, subjecting the stevioside adsorption resin to desorption with an alcohol solution, and collecting the desorbed solution to obtain a stevioside extract; and
4) mixing the post-column solution obtained in processes of adsorption and elution in step 3), adjusting pH of resultant mixed liquid to be acidic, passing the mixed liquid through a chlorogenic acid adsorption resin for adsorption, subjecting the chlorogenic acid adsorption resin to elution with water, subjecting the chlorogenic acid adsorption resin to desorption with an alcohol solution, and collecting the desorbed solution to obtain a chlorogenic acid extract.

Preferably, in the above operation, the high-concentration short-chain alcohol is ethanol with a concentration of 70% to 86%, the organic solvent is n-hexane, the stevioside adsorption resin is T28, and the chlorogenic acid adsorption resin is SP207.

Alternatively, in the above operation, the high-concentration short-chain alcohol is methanol with a concentration of 80% to 96%, the organic solvent is diethyl ether, the stevioside adsorption resin is 201-H, and the chlorogenic acid adsorption resin is 200B.

Alternatively, in the above operation, the high-concentration short-chain alcohol is propanol with a concentration of 70% to 80%, the organic solvent is n-hexane, the stevioside adsorption resin is ADS-750, and the chlorogenic acid adsorption resin is LSA-12.

Preferably, in of the above embodiment, in step 3), the pH is adjusted to 9 to 11, and in step 4), the pH is adjusted to 2 to 3.

As a preferred embodiment, it comprises:
1) extracting *Stevia rebaudiana* powder with an aqueous ethanol solution with a concentration of 84% to 86% to obtain an extract solution;
2) removing the short-chain alcohol in the extract solution by vacuum concentration, subjecting a short-chain alcohol-removed extract solution to liquid-liquid extraction with n-hexane, and taking water layer to obtain a low-polar impurity-removed extract solution;
3) adjusting pH of the low-polar impurity-removed extract solution to 9.8 to 10.2, passing the extract solution through a stevioside adsorption resin for adsorption, subjecting the stevioside adsorption resin to elution with water, subjecting the stevioside adsorption resin to desorption with an alcohol solution, and collecting the desorbed solution to obtain a stevioside extract; and
4) mixing the post-column solution obtained in processes of adsorption and elution in step 3), adjusting pH of resultant mixed liquid to 2.4 to 2.6, passing the mixed liquid through a chlorogenic acid adsorption resin for adsorption, subjecting the chlorogenic acid adsorption resin to elution with water, subjecting the chlorogenic acid adsorption resin to desorption with an alcohol solution, and collecting the desorbed solution to obtain a chlorogenic acid extract.

Preferably, in the above operation, the stevioside adsorption resin is T28; and the chlorogenic acid adsorption resin is SP207.

As a preferred embodiment of operation, the step 3) specifically comprises: adjusting the pH of the low-polar impurity-removed extract solution to 9 to 11, adjusting the solid content of the extract solution to 5% to 10%, passing the extract solution through a stevioside adsorption resin for adsorption with a liquid flow rate controlled to 0.2 to 0.3 BV/h during the adsorption process, then subjecting T28 resin to elution with 2 BV of water with the flow rate of the 1st BV water controlled to 0.2 to 0.4 BV/h and the flow rate of the 2nd BV water controlled to 0.8 to 1 BV/h, and then subjecting the stevioside adsorption resin to desorption with an alcohol solution, and collecting the desorbed solution to obtain the stevioside extract.

As a preferred embodiment of operation, the specific operation for adsorbing chlorogenic acid is as follows:

collecting the post-column solution obtained during the adsorption and water-washing in step 3), adjusting pH of the post-column solution to 2.0 to 3.0, and then passing the resultant solution through the chlorogenic acid adsorption resin for adsorption with the flow rate controlled to 0.8 to 1.2 BV/h during the adsorption process, after the adsorption is completed, washing the resin with 2 BV of water at a flow rate of 0.8 to 1.2 BV/h, and then, subjecting the chlorogenic acid adsorption resin to desorption with an alcohol solution, and collecting the desorbed solution to obtain the chlorogenic acid extract.

As a preferred embodiment of operation, the specific operation for desorption after elution of steviosides and chlorogenic acid extracts is as follows: desorbing the resin with 2 BV of an aqueous ethanol solution with a concentration of 70% to 75% with the flow rate of the ethanol solution controlled to 0.8 to 1.2 BV/h during the desorption.

Another object of the present invention is to protect the chlorogenic acid extract obtained by the method of the present invention;

Preferably, the content of isochlorogenic acid in the chlorogenic acid extract of the present invention is >60%.

The last object of the present invention is to protect the stevioside extract obtained by the method of the present invention;

Preferably, the extract has a total glycoside content of >90%, and a light transmittance of >90 at 420 nm, and the stevioside has a specific absorbance of less than 0.015 at 370 nm under a concentration of 1%.

The present invention has the following beneficial effects:
(1) Compared with the traditional water extraction process, the extraction technology disclosed in the present application can prevent the hydrolysis of the isochlorogenic acid in *Stevia rebaudiana*, so as to ensure the active ingredient content and efficacy of the chlorogenic acid extract of *Stevia rebaudiana*. At the same time, under the above extraction conditions, the simultaneous and effective extraction of steviosides and chlorogenic acid can be realized, and the extraction efficiency in industrial production can be improved.
(2) After the extract is concentrated, liquid-liquid extraction and removal of impurities are carried out to remove low-polar impurities, which can prevent such components from entering the stevioside adsorption resin, improve the efficiency and service life of the stevioside adsorption resin, and increase the purity of the extracted stevioside.
(3) At the same time, the present invention utilizes the acidity of chlorogenic acid. During the process of extracting steviosides, the extract solution is adjusted to alkaline to enable the chlorogenic acid to form into a salt with an increased polarity, so as to achieve effective separation of the chlorogenic acid and glucoside in an adsorption process, which not only improves the quality of stevioside products, but also realizes the effective separation of chlorogenic acid of *Stevia rebaudiana*, and realizes the comprehensive utilization of *Stevia rebaudiana* resources.
(4) The present invention realizes the separation of chlorogenic acid and glycoside through salt formation, and can also improve the purity of chlorogenic acid extract.
(5) Compared with the traditional water extraction process, this process greatly reduces the water consumption during production and reduces the discharge of sewage and flocculation residues, and is a green production process with high efficiency that can greatly promote the progress of the industry.
(6) The stevioside extracted by the present invention has high quality. The extract has a total glycoside content of >90%, a light transmittance of >90 at 420 nm, and the stevioside has a specific absorbance of less than 0.015 at 370 nm under a concentration of 1%. The chlorogenic acid in the chlorogenic acid extract can be better protected, and the isochlorogenic acid content is more than 60%.

DETAILED DESCRIPTION OF THE INVENTION

The following Examples are intended to illustrate the present invention, but are not intended to limit the scope of the present invention.

Example 1

The present Example relates to an industrial utilization method for *Stevia rebaudiana*, which includes the following steps:
(1) 1 kg of *Stevia rebaudiana* powder was weighted, and was subjected to extraction for three times (at a material-liquid ratio of 1:5/3.5/3.5, respectively) at 50° C. with 85% aqueous ethanol as an extracting liquid. The first extraction was performed for 1.5 h, both the second extraction and third extraction were performed for 1 h, and the filtrate was combined as an extract solution.
(2) The extract solution was concentrated to ¹⁄₁₀ of its original volume in a water bath at 60° C. and a vacuum of −0.08 MPa, an equal volume of n-hexane was added to the concentrated solution for liquid-liquid extraction for 3 times, and the water layer was taken to obtain low-polar impurity-removed extract solution.
(3) The pH of the low-polar impurity-removed extract solution was adjusted to 10.0, and the solid content was adjusted to 10%, then the low-polar impurity-removed extract solution was passed through 1.5 L of T28 resin for adsorption, and the liquid flow rate during the adsorption process was adjusted to 0.2 BV/h; After the adsorption was completed, the T28 resin was subjected to elution with 2 BV of water, the flow rate of the 1st BV water was controlled to 0.2 BV/h, and the flow rate of the 2nd BV water was controlled to 1 BV/h. After the elution was completed, the resin was subjected to desorption with 2 BV of 70% aqueous ethanol at a flow rate controlled to 1 BV/h. The desorbed solution was collected, concentrated, desalted, decolorized, refined and dried to obtain 99 g of stevioside product. The product was a white powder with a total glycoside content of 94.5%, a light transmittance of 91.8% at 420 nm, and the stevioside had a specific absorbance of 0.013 at 370 nm under a concentration of 1%.
(4) the post-column solutions obtained from the adsorption and water-washing process were collected, and the pH of the resultant was adjusted to 2.5, and then the resultant was passed through 800 mL of polar sp207 resin for adsorption. The flow rate was controlled to 1 BV/h during the adsorption process. After the adsorption was completed, the resin was subjected to elution with 2 BV of water at a flow rate controlled to 1 BV/h. After the washing with water was completed, the resin was subjected to desorption with 2 BV of 70% aqueous ethanol at a flow rate controlled to 1 BV/h. The desorbed solution was collected, concentrated and dried to obtain 57 g of brown powder. The content of total chlorogenic acid of *Stevia rebaudiana* was 81%, and the content of isochlorogenic acid was 68.49%.

Example 2

The present Example relates to an industrial utilization method for *Stevia rebaudiana*, which includes the following steps:
(1) 1 kg of *Stevia rebaudiana* powder was weighted, and was subjected to extraction twice (at a material-liquid ratio of 1:6/4.5, respectively) at 50° C. with 95% aqueous methanol solution as an extracting liquid. The first extraction was performed for 1.5 h, and the second extraction was performed for 1 h, and the filtrate was combined as an extract solution;
(2) the extract solution was concentrated to ¹/₁₀ of its original volume in a water bath at 60° C. and a vacuum of −0.08 MPa, an equal volume of diethyl ether was added to the concentrated solution for liquid-liquid extraction for 3 times, and the water layer was taken to obtain a low-polar impurity-removed extract solution;
(3) the pH of the low-polar impurity-removed extract solution was adjusted to 9.5, and the solid content was adjusted to 8%, then the low-polar impurity-removed extract solution was passed through 1.5 L of 201-H resin for adsorption, and the liquid flow rate during the adsorption process was adjusted to 0.25 BV/h. After the adsorption was completed, the 201-H resin was subjected to elution with 2 BV of water, the flow rate of the 1st BV water was controlled to 0.25 BV/h, and the flow rate of the 2nd BV water was controlled to 1 BV/h. After the elution was completed, the resin was subjected to desorption with 2 BV of 70% aqueous ethanol at a flow rate controlled to 1 BV/h. The desorbed solution was collected, concentrated, desalted, decolorized, refined and dried to obtain 100.5 g of stevioside product. The product was a white powder with a total glycoside content of 93.9% and a light transmittance of 90.8% at 420 nm, and the stevioside had a specific absorbance of 0.014 at 370 nm under a concentration of 1%.
(4) the post-column solutions obtained from the adsorption and water-washing process were collected, and the pH of the resultant was adjusted to 3.0, and then the resultant was passed through 800 mL of polar 200B resin for adsorption. The flow rate was controlled to 1 BV/h during the adsorption process. After the adsorption was completed, the resin was washed with 2 BV of water at a flow rate controlled to 1 BV/h. After the water-washing was completed, the resin was subjected to desorption with 2 BV of 70% aqueous ethanol at a flow rate controlled to 1 BV/h. The desorbed solution was collected, concentrated and dried to obtain 54 g of brown powder. The content of total chlorogenic acid of *Stevia rebaudiana* was 85.5%, and the content of isochlorogenic acid was 68.9%.

Example 3

The present Example relates to an industrial utilization method for *Stevia rebaudiana*, which includes the following steps:
(1) 1 kg of *Stevia rebaudiana* powder was weighted, and was subjected to extraction for twice (at a material-liquid ratio of 1:6/4.5, respectively) at 50° C. with 75% aqueous propanol solution as an extracting liquid, the first extraction was performed for 1.5 h, the second extraction was performed for 1 h, and the filtrate was combined as an extract solution;
(2) The extract solution was concentrated to ¹/₁₀ of its original volume in a water bath at 60° C. and a vacuum of −0.08 MPa, an equal volume of cyclohexane was added to the concentrated solution for liquid-liquid extraction for 3 times, and the water layer was taken to obtain a low-polar impurity-removed extract solution.
(3) The pH of the low-polar impurity-removed extract solution was adjusted to 9.0, and the solid content was adjusted to 6%, then the low-polar impurity-removed extract solution was passed through 1.5 L of ADS-750 resin for adsorption, and the liquid flow rate during the adsorption process was adjusted to 0.3 BV/h. After the adsorption was completed, the ADS-750 resin was subjected to elution with 2 BV of water, the flow rate of the 1st BV water was controlled to 0.3 BV/h, and the flow rate of the 2nd BV water was controlled to 1 BV/h. After the elution was completed, the resin was subjected to desorption with 2 BV of 70% aqueous ethanol at a flow rate controlled to 1 BV/h. The desorbed solution was collected, concentrated, desalted, decolorized, refined and dried to obtain 99.7 g of stevioside product. The product was a white powder with a total glycoside content of 93.4% and a light transmittance of 90.8% at 420 nm, and the stevioside had a specific absorbance of 0.011 at 370 nm under a concentration of 1%.
(4) The post-column solutions obtained from the adsorption and water-washing process were collected, and the pH of the resultant was adjusted to 2.0, and then the resultant was passed through 800 mL of polar LSA-12 resin for adsorption. The flow rate was controlled to 1 BV/h during the adsorption process. After the adsorption was completed, the resin was washed with 2 BV of water at a flow rate of 1 BV/h. After the washing was completed, the resin was subjected to desorption with 2 BV of 70% aqueous ethanol at a flow rate controlled to 1 BV/h. The desorbed solution was collected, concentrated and dried to obtain 53 g of brown powder. The content of total chlorogenic acid of *Stevia rebaudiana* was 85.1%, and the content of isochlorogenic acid was 69.2%.

Example 4

The present Example relates to an industrial utilization method for *Stevia rebaudiana*, which includes the following steps:
(1) 1 kg of *Stevia rebaudiana* powder was weighted, and was subjected to extraction for three times (at a material-liquid ratio of 1:5/3.5/3.5, respectively) at 60° C. with 70% aqueous ethanol as an extracting liquid. The first extraction was performed for 1.5 h, both the second extraction and third extraction were performed for 1 h, and the filtrate was combined as an extract solution.
(2) The extract solution was concentrated to ¹/₁₀ of its original volume in a water bath at 60° C. and a vacuum of −0.08 MPa, an equal volume of pentane was added to the concentrated solution for liquid-liquid extraction for 3 times, and the water layer was taken to obtain a low-polar impurity-removed extract solution.
(3) The pH of the low-polar impurity-removed extract solution was adjusted to 10.5, and the solid content was adjusted to 6%, then the low-polar impurity-removed extract solution was passed through 1.5 L of T28 resin for adsorption, and the liquid flow rate during the adsorption process was adjusted to 0.3 BV/h. After the adsorption was completed, the T28 resin was subjected to elution with 2 BV of water, the flow rate of the 1st BV water was controlled to 0.3 BV/h, and the flow rate of the 2nd BV water was controlled to 1 BV/h. After the elution was completed, the resin was subjected to desorption with 2 BV of 70% aqueous ethanol at a flow rate controlled to 1 BV/h. The desorbed solution was collected, concentrated, desalted, decolorized, refined and dried to obtain 98.6 g of stevioside product. The product was a white powder with a total glycoside content of 94.7% and a light transmittance of 92.0% at 420 nm, and the stevioside had a specific absorbance of 0.011 at 370 nm under a concentration of 1%.

(4) The post-column solutions obtained from the adsorption and water-washing process were collected, and the pH of the resultant was adjusted to 2.0, and then the resultant was passed through 800 mL of HZ841 resin for adsorption. The flow rate was controlled to 1 BV/h during the adsorption process. After the adsorption was completed, the resin was washed with 2 BV of water at a flow rate of 1 BV/h. After the washing was completed, the resin was subjected to desorption with 2 BV of 70% aqueous ethanol at a flow rate controlled to 1 BV/h. The desorbed solution was collected, concentrated and dried to obtain 55 g of brown powder. The content of total chlorogenic acid of Stevia rebaudiana was 81.1%, and the content of isochlorogenic acid was 65.58%.

Example 5

The present Example relates to an industrial utilization method for Stevia rebaudiana, which includes the following steps:

(1) 1 kg of Stevia rebaudiana powder was weighted, and was subjected to extraction twice (at a material-liquid ratio of 1:6/4.5, respectively) at 55° C. with 80% aqueous methanol solution as an extracting liquid. The first extraction was performed for 1.5 h, the second extraction was performed for 1 h, and the filtrate was combined as an extract solution.

(2) The extract solution was concentrated to ⅒ of its original volume in a water bath at 60° C. and a vacuum of −0.08 MPa, an equal volume of pentane was added to the concentrated solution for liquid-liquid extraction for 3 times, and the water layer was taken to obtain a low-polar impurity-removed extract solution.

(3) The pH of the low-polar impurity-removed extract solution was adjusted to 11.0, and the solid content was adjusted to 6%, then the low-polar impurity-removed extract solution was passed through 1.5 L of 201-H resin for adsorption, and the liquid flow rate during the adsorption process was adjusted to 0.3 BV/h. After the adsorption was completed, the 201-H resin was subjected to elution with 2 BV of water, the flow rate of the 1st BV water was controlled to 0.3 BV/h, and the flow rate of the 2nd BV water was controlled to 1 BV/h. After the elution was completed, the resin was subjected to desorption with 2 BV of 70% aqueous ethanol at a flow rate controlled to 1 BV/h. The desorbed solution was collected, concentrated, desalted, decolorized, refined and dried to obtain 98.2 g of stevioside product. The product was a white powder with a total glycoside content of 95.0% and a light transmittance of 92.5% at 420 nm, and the stevioside had a specific absorbance of 0.010 at 370 nm under a concentration of 1%.

(4) The post-column solutions obtained from the adsorption and washing process were collected, and the pH of the resultant was adjusted to 2.0, and then the resultant was passed through 800 mL of AB-8 resin for adsorption. The flow rate was controlled to 1 BV/h during the adsorption process. After the adsorption was completed, the resin was washed with 2 BV of water at a flow rate controlled to 1 BV/h. After the washing was completed, the resin was subjected to desorption with 2 BV of 70% aqueous ethanol at a flow rate controlled to 1 BV/h. The desorbed solution was collected, concentrated and dried to obtain 56 g of brown powder. The content of total chlorogenic acid of Stevia rebaudiana was 80.1%, and the content of isochlorogenic acid was 64.58%.

Comparative Example 1

In the present Comparative Example, the isochlorogenic acid and stevioside in Stevia rebaudiana was extracted by the water extraction method. The specific operation steps were the method provided in the patent publication No. CN106236808B, and the extracted substances were analyzed by liquid chromatography.

The chlorogenic acid in the raw material of Stevia rebaudiana (Gansu seedlings) and the chlorogenic acid in the extract solution of Example 1 were analyzed by liquid chromatography, and compared with monomers in the extract solution of Comparative Example 1. The results were shown in the table 1:

TABLE 1

| Proportion of stevia rebaudiana isochlorogenic acid and related components accounted for in total chlorogenic acid | Raw materials | Water extract | Extract solution in Example 1 |
|---|---|---|---|
| Mono-caffeoyl substituted chlorogenic acid/% | 20.23 | 38.73 | 13.84 |
| Caffeic acid/% | 0.44 | 14.83 | 0.27 |
| Isochlorogenic acid/% | 79.33 | 45.07 | 85.89 |

It can be seen from the data in Table 1 that, compared with the chlorogenic acid in the raw materials, the proportion of isochlorogenic acid in the extract solution obtained in Comparative Example 1 decreased from 79.33% to 45.07%, and the proportion of caffeic acid (complete hydrolysate of isochlorogenic acid) increased from 0.44% to 14.83%, and the proportion of mono-caffeoyl substituted chlorogenic acid (produced by partial incomplete hydrolysis of isochlorogenic acid) increased, indicating that isochlorogenic acid was degraded during the extraction process (it was confirmed by the content detection of the extracted residue that the total chlorogenic acid was completely extracted), and the proportions of each component in the extract solution obtained in Example 1 were close to those of the raw material, and the isochlorogenic acid component was stable during the extraction process.

Comparative Example 2

The present Comparative Example is the same as Example 1 except that the extracting liquid was 65% aqueous ethanol. 103.5 g of steviosides were obtained by extraction. The product was a white powder with a total glycoside content of 90.1% and a light transmittance of 80.2% at 420 nm, and the stevioside had a specific absorbance of 0.033 at 370 nm under a concentration of 1%. 59.3 g of brown powder of chlorogenic acid was obtained by extraction, in which the total chlorogenic acid of Stevia rebaudiana was 74%, and the content of isochlorogenic acid was 52.8%.

Comparative Example 3

The present Comparative Example is the same as Example 1 except that in step 2), liquid-liquid extraction and removal of impurities were not performed. 107.2 g of steviosides were obtained by extraction. The product was a white powder with a total glycoside content of 87.3% and a light transmittance of 74% at 420 nm, and the stevioside had a specific absorbance of 0.045 at 370 nm under a concentration of 1%. 61.7 g of brown powder of chlorogenic acid was obtained by extraction, in which the total chlorogenic acid of Stevia rebaudiana was 71%, and the content of isochlorogenic acid was 56.9%.

Comparative Example 4

The present Comparative Example is the same as Example 1 except that in step 3), the pH of the extract solution was not adjusted before loading. 110.3 g of steviosides were obtained by extraction. The product was a white powder with a total glycoside content of 84.9% and a light transmittance of 70% at 420 nm, and the stevioside had a specific absorbance of 0.053 at 370 nm under a concentration of 1%. 12.5 g of brown powder of chlorogenic acid was obtained by extraction, in which the total chlorogenic acid of Stevia rebaudiana was 71%, and the content of isochlorogenic acid was 54.3%.

It can be seen from Comparative Examples 2 to 4 that the total glycoside content of the steviosides obtained by extraction without the method of the present application is lower, and the measured values of light transmittance and specific absorption are also significantly increased, which proves that the purity and quality of the obtained product are significantly lower than that of the present application.

The total glycoside content in the present application is determined by the GB 8270-2014 method, the light transmittance is a light transmittance at 420 nm is detected by UV at a solid content of 14%, and the specific absorbance of steviosides at 370 nm under a concentration of 1% was determined by the GB 8270-1999 method, and the content of total chlorogenic acid and the ratio of each component were determined by the T/CCCMHPIE 1.17-2016 method.

Although a general description, specific embodiments and experiments have been used to describe the present invention in detail above, it is obvious to those skilled in the art that some modifications or improvements can be made on the basis of the present invention. Therefore, all these modifications or improvements made without departing from the spirit of the present invention fall within the protection scope of the present invention.

INDUSTRIAL APPLICABILITY

The invention provides an industrialization method for comprehensive utilization of Stevia rebaudiana. The method of the present invention mainly comprises: the Stevia rebaudiana is extracted using a high-concentration alcohol solution, then the extracted solution is purified using an organic solvent, and the pH of the extracted solution is adjusted to be alkaline according to the acidic characteristic of chlorogenic acid to enable the chlorogenic acid to form into a salt with an increased polarity so as to achieve effective separation of the chlorogenic acid from glucoside components in an adsorption process. The method allows the high-quality stevioside and chlorogenic acid to be obtained, significantly improves the comprehensive utilization ratio of Stevia rebaudiana, reduces the waste of natural Stevia rebaudiana resources, reduces the resource consumption in the production process and reduces waste discharge. It is a high-benefit green production process, and has good economic value and application prospects.

We claim:

1. An industrial utilization method for extracting Stevia rebaudiana, comprising:
    1) Extracting Stevia rebaudiana powder with a high-concentration short-chain alcohol aqueous solution to obtain an extract solution, wherein the short-chain alcohol in the high-concentration short-chain alcohol aqueous solution is selected from methanol, ethanol, propanol or any combination thereof, and a volume fraction of the short-chain alcohol in the short-chain alcohol aqueous solution is 70% to 95%;
    2) Removing the short-chain alcohol in the extract solution by vacuum concentration, and subjecting the extract solution to liquid-liquid extraction with an organic solvent, and taking water layer to obtain a low-polar impurity-removed extract solution, wherein the organic solvent is a low-polar organic solvent that is water insoluble; and
    3) Adjusting pH of the low-polar impurity-removed extract solution to be alkaline, and passing the extract solution through a stevioside adsorption resin to obtain a stevioside extract.

2. The method according to claim 1, wherein the method comprises adjusting pH of a post-column solution obtained by passing the low-polar impurity-removed extract solution through a stevioside resin to be acidic, and passing the post-column solution through a chlorogenic acid adsorption resin to obtain a chlorogenic acid extract.

3. The method according to claim 2, wherein the organic solvent is selected from the group of pentane, n-hexane, octane, diethyl ether or cyclohexane.

4. The method according to claim 2, wherein the pH of the post-column solution obtained by passing the low-polar impurity-removed extract solution through a stevioside resin is adjusted to 2 to 3.

5. The method according to claim 1, wherein the Stevia rebaudiana extraction is performed at a material-liquid ratio of 1:3.5 to 1:6, and an extraction temperature of 20° C. to 80° C.; and/or the extraction is performed for 2 to 3 times with 0.5 h to 3 h for each extraction.

6. The method according to claim 2, further comprising:
    removing the short-chain alcohol in the extract solution by vacuum concentration;
    subjecting the stevioside adsorption resin to elution with water, subjecting the stevioside adsorption resin to desorption with an alcohol solution, and collecting the desorbed solution to obtain a stevioside extract; and
    mixing the post-column solution, adjusting pH of resultant mixed liquid to be acidic, passing the mixed liquid through a chlorogenic acid adsorption resin for adsorption, subjecting the chlorogenic acid adsorption resin to elution with water, and subjecting the chlorogenic acid adsorption resin to desorption with an alcohol solution, and collecting the desorbed solution to obtain a chlorogenic acid extract.

7. The method according to claim 2, wherein the organic solvent is a low-polar organic solvent that is water insoluble, selected from the group of pentane, n-hexane, octane, diethyl ether or cyclohexane.

8. The method according to claim 2, wherein in the step 3), the pH of the low-polar impurity-removed extract solution is adjusted to 9 to 11.

9. The method according to claim 1, wherein in the step 3), the pH of the low-polar impurity-removed extract solution is adjusted to 9 to 11.

10. The method according to claim 3, wherein in the step 3), the pH of the low-polar impurity-removed extract solution is adjusted to 9 to 11.

11. The method according to claim 3, wherein the pH of the post-column solution obtained by passing the low-polar impurity-removed extract solution through a stevioside resin is adjusted to 2 to 3.

12. The method according to claim 2, wherein the *Stevia rebaudiana* extraction is performed at a material-liquid ratio of 1:3.5 to 1:6, and an extraction temperature of 20° C. to 80° C.; and/or the extraction is performed for 2 to 3 times with 0.5 h to 3 h for each extraction.

\* \* \* \* \*